United States Patent
Riederer et al.

(10) Patent No.: US 11,406,277 B2
(45) Date of Patent: Aug. 9, 2022

(54) METHODS FOR DETERMINING CONTRAST AGENT CONCENTRATION USING MAGNETIC RESONANCE IMAGING

(71) Applicant: Mayo Foundation for Medical Education and Research, Rochester, MN (US)

(72) Inventors: Stephen J. Riederer, Rochester, MN (US); Eric G. Stinson, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 358 days.

(21) Appl. No.: 16/606,140

(22) PCT Filed: Apr. 19, 2018

(86) PCT No.: PCT/US2018/028319
§ 371 (c)(1),
(2) Date: Oct. 17, 2019

(87) PCT Pub. No.: WO2018/195287
PCT Pub. Date: Oct. 25, 2018

(65) Prior Publication Data
US 2020/0069216 A1    Mar. 5, 2020

Related U.S. Application Data

(60) Provisional application No. 62/487,845, filed on Apr. 20, 2017.

(51) Int. Cl.
*A61B 5/055* (2006.01)
*G01R 33/48* (2006.01)
(Continued)

(52) U.S. Cl.
CPC ............ *A61B 5/055* (2013.01); *G01R 33/485* (2013.01); *G01R 33/4828* (2013.01); *G01R 33/5601* (2013.01); *G01R 33/5608* (2013.01)

(58) Field of Classification Search
CPC .. A61B 5/055; G01R 33/4828; G01R 33/485; G01R 33/5601; G01R 33/5608
See application file for complete search history.

(56) References Cited

PUBLICATIONS

Ribot et al. ("Application of MRI phase-difference mapping to assessment of vascular concentrations of BMS agent in mice". Contrast Media Mol. Imaging 2007. pp. 64-71). (Year: 2007).*

(Continued)

*Primary Examiner* — Amanda Lauritzen Moher
*Assistant Examiner* — Delia M. Appiah Mensah
(74) *Attorney, Agent, or Firm* — Quarles & Brady LLP (57) ABSTRACT

The present disclosure provides systems and methods for measuring a concentration of a contrast agent using magnetic resonance imaging (MRI). The method includes acquiring pre- and post-contrast data from a volume of a subject, where the pre-contrast data is acquired before a contrast agent is administered and the post-contrast data is acquired after the contrast agent is administered. Pre- and post-contrast resonance frequency maps are then computed, where the pre-contrast frequency map is based on one or more pre-contrast resonance frequency values, and the post-contrast resonance frequency map is based on one or more post-contrast resonance frequency values. The pre- and post-contrast frequency maps are then used to generate a resonance frequency change map that is subsequently used to generate a contrast agent concentration map that indicates a concentration of the contrast agent that was present at each voxel in the volume at the second time.

17 Claims, 4 Drawing Sheets

(51) Int. Cl.
  *G01R 33/485* (2006.01)
  *G01R 33/56* (2006.01)

(56) References Cited

PUBLICATIONS

Ma ("Dixon Techniques for Water and Fat Imaging". Journal of Magnetic Resonance Imaging. 2008. pp. 543-558). (Year: 2008).*
Sengpiel ("Phase in Acoustics". Apr. 2007. p. 2). (Year: 2007).*
International Search Report and Written Opinion from parent PCT/US2018/028319, dated Aug. 13, 2018, 14 pages.
Ribot, et al., Application of MRI phase-difference mapping to assessment of vascular concentrations of BMS agent in mice, Contrast Media & Molecular Imaging, vol. 3, No. 2, Mar. 28, 2008, pp. 64-71.
Ma, Dixon techniques for water and fat imaging, Journal of Magnetic Resonance Imaging, Society for Magnetic Resonance Imaging, Oak Brook, IL, US, vol. 28, No. 3, Sep. 5, 2008, pp. 543-558.
Stinson, et al., Effect of Gadolinium-Induced Susceptibility on First-Pass Single-echo Dixon CE-MRA and Methods for Correction, Proceedings of the International Society for Magnetic Resonance in Medicine, ISMRM, 24th Annual Meeting and Exhibition, Singapore, May 7-May 13, 2016, No. 2673, Apr. 22, 2016, 3 pages.
Stinson, et al., Time-Resolved Contrast-Enhanced MR Angiography with Single-Echo Dixon Background Suppression, Proceedings of the International Society for Magnetic Resonance in Medicine, ISMRM, 25th Annual Meeting and Exhibition, Honolulu, HI, USA, Apr. 22-Apr. 27, 2017, No. 3264, Apr. 7, 2017, 3 pages.

* cited by examiner

METHODS FOR DETERMINING CONTRAST AGENT CONCENTRATION USING MAGNETIC RESONANCE IMAGING

CROSS-REFERENCE TO RELATED APPLICATIONS

This application is a U.S. 371 National Phase Entry of PCT/US2018/028319, filed Apr. 19, 2018, which claims the benefit of U.S. Provisional Patent Application Ser. No. 62/487,845, filed on Apr. 20, 2017, and entitled "GADO-LINIUM-INDUCED SUSCEPTIBILITY EFFECTS IN SINGLE-ECHO DIXON CE-MRA," each of which is herein incorporated by reference in its entirety.

STATEMENT REGARDING FEDERALLY SPONSORED RESEARCH

This invention was made with government support under EB000212 awarded by the National Institutes of Health. The government has certain rights in the invention.

BACKGROUND

Contrast agents are used in many imaging modalities for a variety of purposes. They are generally administered in some fashion and then selectively flow to or are taken up by specific tissues, organs, or cell types within the body. Sometime after administration the distribution of the contrast agent is imaged using a specific modality such as nuclear medicine, computed tomography (CT), or magnetic resonance imaging (MRI). As one example, contrast agents can be used to highlight the blood within the body's vasculature. In such instances, the contrast agent is often administered intravenously as a bolus injection, such as into a vein in the arm.

For CT, the contrast agent typically contains iodine (I) because it is relatively opaque to x-rays. The volume of contrast material or "bolus" can be as large as 100 ml. For MRI, the contrast agent typically is based on gadolinium (Gd) because it causes a shortening of the T1 relaxation time. Agents based on other elements, such as iron (Fe) or manganese (Mn), are also used in MRI. The bolus volume is generally no larger than 20 ml.

The contrast agent is initially very concentrated at the site of injection but then becomes progressively diluted as it mixes with blood, first in the venous path from the injection site to the right atrium and ventricle of the heart, then within the pulmonary circulation, and finally within the left atrium and ventricle of the heart before going to the arterial circulation. Although it can be highly variable from subject subject, the level of dilution of the contrast bolus from the injection site to the arterial circulation is in the range of a factor of 10 to 100. If the contrast agent bolus volume is administered over a time period of five to ten seconds, then importantly, in spite of the dilution, there will generally still be a clear "first pass" of the washin and washout of contrast-enhanced blood at any artery, the first pass lasting the order of 10 to 30 seconds.

Contrast agents are commonly used in a qualitative manner. That is, an image of the presence or absence of contrast-enhanced blood within some vascular territory can provide valuable information about which blood vessels fill and which ones do not. However, contrast agents can potentially be used in a quantitative manner as well. One way is to simply note the arrival time of contrast-enhanced blood in some target vessel after the initiation of injection. More sophisticated uses are also possible.

One non-limiting example of a quantitative usage of contrast enhancement is quantitative perfusion imaging, particularly for diagnosing cancer. In this case the clinician wishes to determine the rate at which blood is taken up by a possible malignancy as well as the rate of washout. For malignancies both of these rates are often very rapid. However, to normalize the observed behavior from one lesion to another it is generally desirable to relate the observed enhancement to the blood flow in the artery which is supplying blood to the suspect lesion. This can be done using various perfusion models, such as those of Kety (Pharmacol Rev. 1951; 3: 1-41), Tofts (J. Magn. Reson. Img. 1999; 10: 223-232), and others. Such models, however, require that the concentration of contrast material in the various blood vessels and organs, referred to more generally as "compartments," be known quantitatively.

For CT imaging the reconstructed signal at a voxel is a measure of x-ray attenuation occurring in that voxel. The increase in attenuation due to the presence of iodinated contrast material is essentially proportional to the iodine concentration. This simplifies the usage of CT-derived measurements in quantitative measurements of perfusion. With MRI on the other hand, the relationship of the reconstructed MRI signal to the concentration of contrast-agent in a voxel is far more complicated, and there remains a need for simplifying these calculations in order to make quantitative perfusion using MRI much more accessible.

As stated previously, Gd-based contrast agents are effective in MRI because of their effect in increasing the relaxation rate, or decreasing the T1 relaxation time (in sec or msec), of the surrounding hydrogen nuclei. Gradient echo acquisitions are an example of pulse sequences that can often be used to visualize Gd-based agents with MRI. The signal S(t) in gradient echo acquisition is dependent on relaxation time T1 and is given by:

$$S(t) = M_0 \frac{1 - e^{-TR/T1}}{1 - \cos(\alpha)e^{-TR/T1}} e^{-t/T2^*} \sin(\alpha); \qquad (1)$$

If some tissue enhances due to the presence of contrast material, then its enhanced T1 is related to $T1_0$, its T1 value prior to contrast arrival, by:

$$\frac{1}{T1} = \frac{1}{T1_0} + R \cdot [Gd]; \qquad (2)$$

where R is the "relaxivity" of the specific contrast agent being used in units of $(mM \cdot sec)^{-1}$, and [Gd] is the concentration of the assumed Gd-based contrast agent, measured in mM (millimolar, or mmol/L).

To model perfusion with the above-described quantitative methods it is necessary to determine the concentration of the contrast agent, [Gd]. This requires multiple steps or assumptions. Using Eqn. (2) as a reference, first, the relaxivity must be known. There can be uncertainty in this value, often at the level of five percent or more. Next, the unenhanced T1 value, $T1_0$, needs to be known or determined. For clinical MRI examinations this is generally not done. It is possible to apply multiple pulse sequences to determine $T1_0$ or to assume some typical, population-based value, but these values may introduce error as they are not patient specific.

Next, the enhanced T1 value needs to be determined. Referring back to Eqn. (1), this can be done by applying the pulse sequence using different RF flip angles (α) and estimating T1 from the multiple signals. However, this assumes that the flip angles assumed in the equation used for estimation actually match those applied in the MRI acquisition. Reconciling these often requires additional calibration scans to determine accurate transmission RF (B1) profiles. Also, depending upon the actual level of the contrast agent, the T2*relaxation time may also become shortened so that it too needs to be accounted for. To summarize, this process of determining contrast agent concentration (e.g., [Gd]) requires multiple steps and additional scans beyond those used to simply visualize the uptake of the Gd-based contrast agent as is done for routine clinical scanning.

Currently, there is a need in the art for simplifying the process for quantitatively determining the concentration of Gd-based contrast agents, other paramagnetic contrast agents, superparamagnetic contrast agents, or other contrast agents that affect the longitudinal relaxation, transverse relaxation, or both, of nuclear spin species using MRI signals.

SUMMARY OF THE DISCLOSURE

The present disclosure addresses the aforementioned drawbacks by providing a method for measuring a concentration of a contrast agent using magnetic resonance imaging ("MRI"). Pre-contrast data that were acquired from a volume using an MRI system at a first time occurring before a contrast agent was present in the volume are provided to a computer system. Post-contrast data that were acquired from the volume using the MRI system at a second time occurring when the contrast agent was present in the volume are also provided to the computer system. A pre-contrast resonance frequency map containing voxels having values indicating first resonance frequency values for each voxel in the volume is computed from the pre-contrast data with the computer system. A post-contrast resonance frequency map containing voxels having values indicating second resonance frequency values for each voxel in the volume is computed from the post-contrast data with the computer system. A resonance frequency change map containing voxels having values indicating a difference between the first resonance frequency and the second resonance frequency measured at that voxel is computed with the computer system. From the resonance frequency change map, a contrast agent concentration map containing voxels that indicate a concentration of the contrast agent that was present at each voxel in the volume at the second time is generated.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are methods for measuring or otherwise determining the concentration (e.g., the absolute concentration) of a contrast agent using magnetic resonance imaging ("MRI"). As stated above, contrast agents used in MRI typically change the relaxation rate of the spins that are proximate to the contrast agent. As one non-limiting example, the contrast agent can be a gadolinium ("Gd") based contrast agent, which increases the longitudinal relaxation rate (R1), or decreases the longitudinal relaxation time (T1), of the surrounding spins, which may be hydrogen nuclei or other spins from which magnetic resonance signals are to be obtained. In other examples, the contrast agent can include other paramagnetic contrast agents (e.g., manganese based agents), superparamagnetic materials (e.g., superparamagnetic iron oxide based agents), or other contrast agents that affect the longitudinal relaxation, transverse relaxation, or both, of nuclear spins.

Rather than estimate the concentration of the contrast agent from the change in the longitudinal relaxation time T1, the methods described in the present disclosure measure or otherwise determine the intrinsic change in resonance frequency of the spins caused by the contrast agent. Although this change in frequency is small (e.g., on the order of 10 Hz per mM of contrast agent), it is measurable using the methods described in the present disclosure.

In general, the methods described in the present disclosure include acquiring pre-contrast data from a volume prior to the arrival of a contrast agent and post-contrast data from the volume when the contrast agent is present in the volume. The resonance frequency in each voxel in the pre-contrast state is measured using the pre-contrast data, and the resonance frequency in each voxel in the post-contrast state is measured using the post-contrast data. The change in resonance frequency between the pre-contrast and post-contrast states is computed and converted to concentration in order to directly measure, or otherwise determine, the concentration of the contrast agent that was present when the post-contrast data were acquired. Mathematically, the theory of measurement may be explained, without limiting the disclosure, as follows:

As stated above, the method relies upon knowledge of the resonance frequency at each voxel prior to arrival of contrast material. This can be measured by expressing the signal in the voxel as a function of those quantities that can affect the resonance frequency, and thereby the phase, as a function of time, which may be defined as the time, t, after excitation by an RF pulse, $$G(t) = (We^{i\phi_W} + Fe^{i\phi_F}e^{i\theta(t)})e^{i\phi(t)} \quad (3);$$

where $G(t)$ is the measured (complex-valued) signal at time t, $W$ and $\phi_W$ are the real-valued magnitude and phase of the complex water magnetization after excitation, $F$ and $\phi_F$ the analogous real-valued magnitude and phase for fat, $\theta(t)$ is the phase accumulation of fat due to its chemical shift with respect to water, and $\phi(t) = \gamma \Delta B_0 t$ is the phase accumulation due to the assumed inhomogeneity $\Delta B_0$ in the principal magnetic field $B_0$. Also, $\gamma$ is the gyromagnetic ratio, which is approximately 42.58 MHz/Tesla for protons. In Eqn. (3), it can be assumed that $\theta(t) = 2\pi \Delta F t$ is known because the fat-water chemical shift frequency difference, $\Delta F$, is known. This leaves five real-valued unknowns, which can be determined from three complex measurements (e.g., measurements having real and imaginary parts).

The above can be simplified by making the assumption that water and fat have the same shared phase $\phi_0$ immediately after excitation; i.e. $\phi_W = \phi_F = \phi_0$. This recasts Eqn. (3) into:

$$G(t) = (W + Fe^{i\theta(t)})e^{i(\phi(t)+\phi_0)} \quad (4).$$

With this approach it is possible to determine the resultant four real-valued unknown quantities ($W$, $F$, $\phi_0$, $\Delta B_0$) by using at least two complex measurements. The two complex measurements may be acquired with a gradient-echo, or other suitable, pulse sequence that is designed to acquire pre-contrast data composed of at least two signals at two different echo times, $G(TE1)$ and $G(TE2)$. Although not necessary, the results may be improved in some instances if the phase angle between the water and fat magnetizations has an approximate n radians difference for the two echo times used. Expressed another way, if the measurements $G(t)$ of Eqn. (4) are made at $t=TE1$ and $TE2$, where $TE1$ and $TE2$ are the first and second echo times of the presumed gradient echo sequence, then:

$$TE2 - TE1 = \frac{n_{odd}}{2 \cdot \Delta F}; \quad (5)$$

where $n_{odd}$ is an odd integer.

In some aspects, the two measurements $G(TE1)$ and $G(TE2)$ can be acquired using a dual-echo pulse sequence. That is to say, a single repetition of the gradient echo, or other suitable, pulse sequence can be designed to acquire two signals at different echo times in a given repetition time ("TR") period. If desired, it is also possible to acquire $G(TE1)$ and $G(TE2)$ in separate repetitions (i.e., in different TR periods).

In one non-limiting example, the pre-contrast calibration information is acquired and used to determine the four unknowns of Eqn. (4) using a Dixon-type method, such as a single-echo Dixon method or a multi-echo Dixon method. A suitable example includes a constrained-phase dual-echo Dixon imaging method with regularized graph-cuts-guided optimization, such as that described by E. G. Stinson, et al., in "Dual Echo Dixon Imaging with Constrained Phase Signal Model and Graph Cuts Reconstruction," *Magnetic Resonance in Medicine,* 2017; 78:2203-2215, which is incorporated herein by reference.

Once the pre-contrast information is collected, the contrast agent can be administered and the post-contrast signal measured. The post-contrast signal behaves according to the following equation:

$$G(t) = (W'e^{i\Delta\phi_{opt}(t)} + Fe^{i\theta(t)})e^{i(\phi(t)+\phi_0)} \quad (6).$$

Compared to Eqn. (4), this equation allows for the water magnetization magnitude to be changed (generally increased) from $W$ to $W'$ due to T1-related effects of the contrast agent. There is an additional term, $\exp(i\Delta\phi_{opt}(t))$, applied to the water magnitude $W'$ that allows for incremental phase accumulation beyond that determined in the multi-echo calibration. All other terms in Eqn. (6), specifically $\phi(t) = \gamma \Delta B_0 t$, $\phi_0$, and $\theta(t)$, may be considered to be known from data acquisition that are acquired using, for example, a single-echo contrast enhanced acquisition, or multi-echo contrast enhanced acquisition, or from a pre-contrast multi-echo acquisition. It may be assumed in Eqn. (6) that the contrast material does not alter the magnitude or phase of the fat.

The phase $\Delta\phi_{opt}(t)$ is not known because the concentration [Gd] is not known. However, the phase can be determined by iteratively applying a trial phase value $\Delta\phi_{test}$ to the water channel and noting which value approximately or exactly compensates for $\Delta\phi_{opt}(t)$ and maximizes the resultant water magnitude, as will be further explained.

Once the phase $\Delta\phi_{opt}(t)$ is known from the above process, it can be converted to offset frequency (f) according to:

$$f = \frac{\Delta\phi_{opt}(t)}{2\pi \cdot t}; \quad (7)$$

where t is the echo time used for $G(t)$ of Eqn. (6). Offset frequency (f) can then be converted to concentration [Gd] using pre-determined calibration data, as will be further described below.

Figure 1:
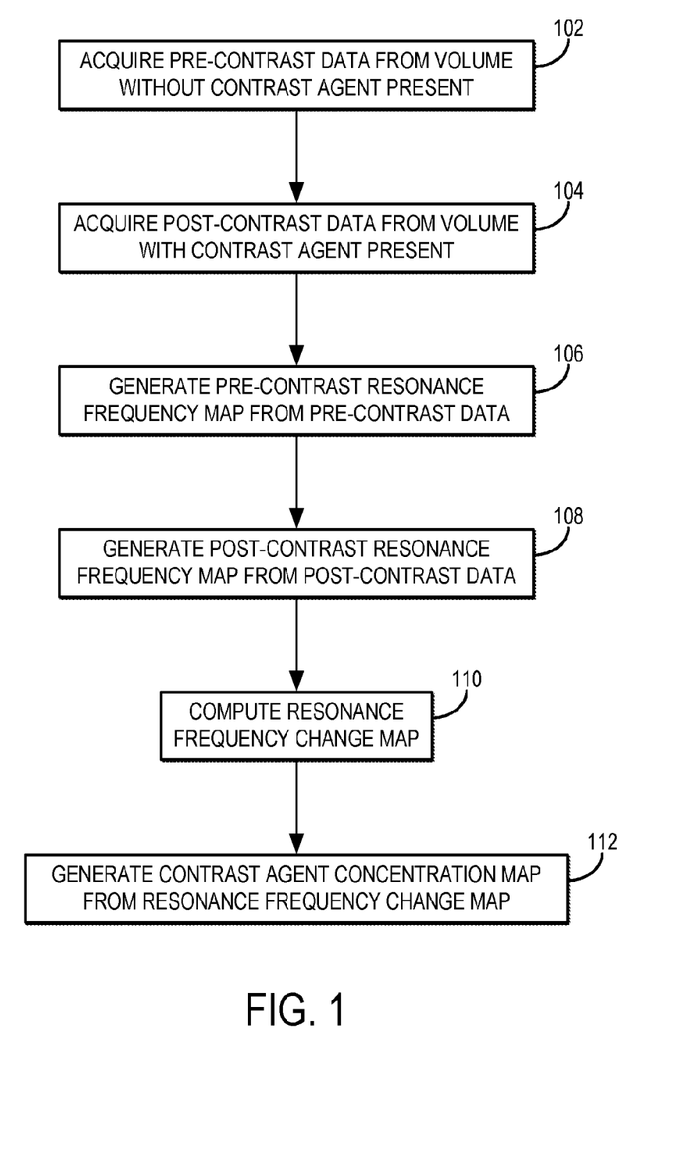
FIG. 1 is a flowchart setting forth the steps of a method for determining a contrast agent concentration in accordance with an embodiment described in the present disclosure.

Referring now to FIG. 1, a flowchart is illustrated as setting forth the steps of an example method for measuring the concentration of a contrast agent using MRI. The method includes providing pre-contrast data to a computer system, as indicated at step 102. The pre-contrast data can be provided to the computer system by retrieving previously acquired data from a memory or other data storage device. The pre-contrast data can also be provided to the computer system by acquiring the data using an MRI system and communicating the acquired data to the computer system, which may form a part of the MRI system. In general, the pre-contrast data includes data acquired from a volume with the MRI system at a first time point during which a contrast agent is not present in the volume. For instance, the pre-contrast data can be data acquired from a volume in a subject before a contrast agent has been administered to the subject.

The method also includes providing post-contrast data to a computer system, as indicated at step 104. The post-contrast data can be provided to the computer system by retrieving previously acquired data from a memory or other data storage device. The post-contrast data can also be provided to the computer system by acquiring the data using an MRI system and communicating the acquired data to the computer system, which may form a part of the MRI system. In general, the post-contrast data includes data acquired from the same volume as the pre-contrast data with the MRI system at a second time point during which a contrast agent is present in the volume. For instance, the post-contrast data can be data acquired from the volume in the subject after the contrast agent has been administered to the subject and arrived in the volume.

In some embodiments, the pre-contrast data and the post-contrast data can be acquired with the MRI system using a gradient echo pulse sequence. Suitable gradient echo pulse sequences may include, but are not limited to single-echo Dixon-type methods or multi-echo Dixon-type methods. Multi-echo Dixon methods have gained interest in contrast-enhanced MR angiography (CE-MRA) because they avoid misregistration-based subtraction artifacts and improve signal-to-noise-ratio as compared to conventional time-subtraction methods. However, multi-echo Dixon methods have additional data requirements of multi-echo imaging and can have increased scan time or reduced temporal or spatial resolution. If initial phase $\phi_0$ and $\Delta B_0$-induced phase $\phi(t)$ are known a priori, single-echo Dixon methods can provide the same benefits, without the trade-offs. Single-echo Dixon imaging is particularly effective in time-resolved studies, where the additional calibration time needed to estimate $\phi_0$ and $\phi(t)$ may be performed once in a calibration scan and amortized over numerous time points.

As indicated by process block 106, a pre-contrast resonance frequency map is then computed based on the unknown pre-contrast resonance frequency values. As shown in Eqn. (3), the pre-contrast data signal includes four real-valued unknown values (W, F, $\phi_0$, $\Delta B_0$) that may be used to generate a pre-contrast resonance frequency map. In some aspects, the unknown resonance frequency values may be determined by acquiring at least two measurements: one at a first echo time G(TE1) and one a second echo time G(TE2). The two measurements may be acquired using a single repetition of the gradient echo, or other suitable, pulse sequence to acquire the two measurements at different echo times. Additionally or alternatively, the two measurements G(TE1) and G(TE2) are acquired in separate repetitions.

Figure 2A:
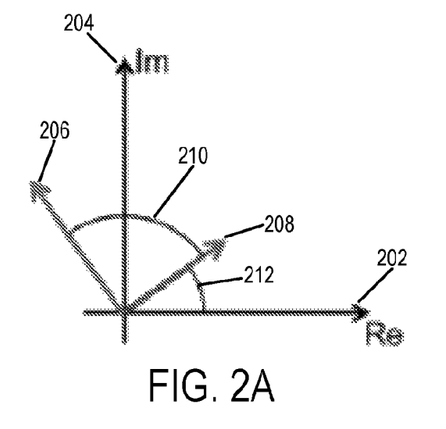
FIG. 2 is a graphical illustration of an example method for determining resonance frequency parameters from pre-contrast data in accordance with an embodiments described in the present disclosure.
Figure 2B:
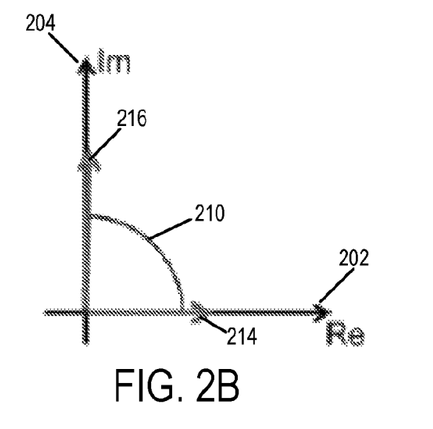

Referring to FIGS. 2A and 2B, a graphical illustration is provided to show a method of determining the unknown pre-contrast resonance frequency values from the acquired pre-contrast data. FIG. 2A is a graphical illustration of the complex magnetization of the acquired pre-contrast data, where the graph includes a real axis 202 and an imaginary axis 204. The acquired pre-contrast data includes an initial pre-contrast fat (F) magnitude 206, an initial pre-contrast water (W) magnitude 208, phase accumulation $\theta(t)$ of fat due to its chemical shift with respect to water 210, a pre-contrast fat phase or the pre-contrast water phase ($\phi_0$) and a phase accumulation due to field inhomogeneity $\phi(t)$ that may be combined ($\phi_0+\phi(t)$) to form the phase signal observed at 212. In some aspects, it may be assumed that water and fat have the same shared initial phase $\phi_0$ immediately after excitation, i.e., $\phi_W=\phi_F=\phi_0$. The phase accumulation $\theta(t)$ is considered to be known, and can be based on operator input specification. The phase accumulation due to field inhomogeneity is related to the unknown $\Delta B_0$ through the previously mentioned relationship, $\phi(t)=\gamma\Delta B_0 t$.

The unknown pre-contrast resonance frequency values may then be determined through a reconstruction process, as described above, and shown graphically in FIG. 2B. During the reconstruction process, the pre-contrast water (W) magnitude 208 may be estimated by demodulating or accounting for the known phase ($\phi_0+\phi(t)$). That is, the initial pre-contrast water (W) magnitude 208 may be projected onto the real axis 202 such that the phase 212 attributed to the accumulation due to field inhomogeneity $\phi(t)$ and the pre-contrast water phase $\phi_0$ are demodulated. The magnitude of the resultant real component vector is taken as an estimate for the pre-contrast water (W) magnitude 214. In the reconstruction process, the initial pre-contrast fat (F) magnitude 206 is also projected onto the imaginary axis 204, and the resultant imaginary component vector may be taken as an estimate for the pre-contrast fat (F) magnitude 216.

Referring back to FIG. 1, as indicated by process block 108, a post-contrast resonance frequency map is then computed based on one or more of the unknown post-contrast resonance frequency values. Similar to above, FIGS. 3A and 3B provide a graphical illustration to show a method of determining the unknown post-contrast resonance frequency values from the acquired complex post-contrast data, where the graph includes a real axis 302 and an imaginary axis 304.

Figure 3A:
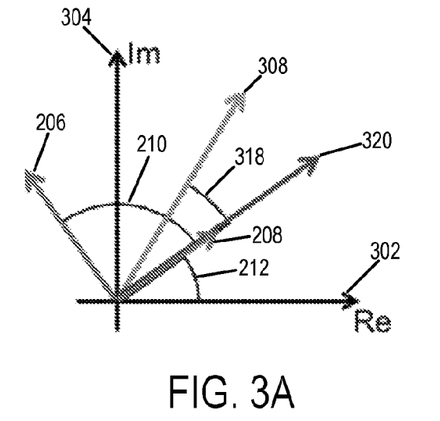
FIG. 3 is a graphical illustration of an example method for determining resonance frequency parameters from post-contrast data in accordance with an embodiments described in the present disclosure.

As shown in FIG. 3A, the acquired post-contrast data can include some similar, or identical, parameters that do not significantly change between pre- and post-contrast acquisitions (e.g., F, $\phi_0$, $\Delta B_0$, and $\phi(t)$ do not change significantly, and $\theta(t)$ is known). For example, FIG. 3A includes an initial post-contrast fat (F) magnitude 206, a post-contrast water phase $\phi_0$ and a phase accumulation due to field inhomogeneity $\phi(t)$ that are combined ($\phi_0+\phi(t)$) to form a phase signal 212, and a phase accumulation $\theta(t)$ of fat due to its chemical shift with respect to water 210. Additionally, the post-contrast data includes unknown post-contrast resonance frequency parameters that do change between pre- and post-contrast acquisitions. In the post-contrast data, the water signal may change both in magnitude and in phase due to the presence of the contrast agent. For example, as shown graphically in FIG. 3A, the pre-contrast water (W) magnitude 208 may be increased to an initial post-contrast water (W') magnitude 308 due to the T1 shortening effects of the contrast agent. Additionally, the contrast agent will typically cause a slight change in the resonance frequency of water $\Delta\phi_{opt}(t)$, as shown in FIG. 3A by the additional phase 318. The additional phase 318 causes the initial post-contrast water (W') magnitude 308 to be shifted from its initial direction parallel with the initial pre-contrast water (W) magnitude 208. For comparison, an estimated post-contrast water (W'$_{est}$) magnitude 320 is provided in FIG. 3A that illustrates the post-contrast water magnitude without the additional phase 318 shift.

Figure 3B:
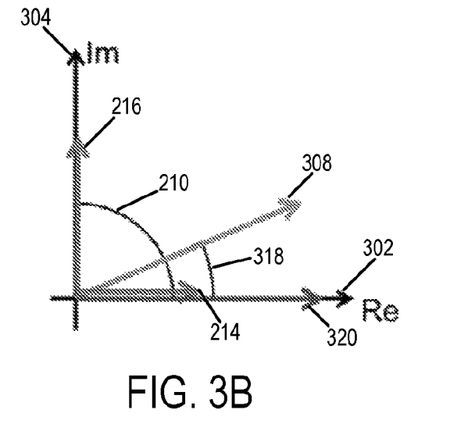

Referring to FIG. 3B, the unknown post-contrast resonance frequency values, W' and $\Delta\phi_{opt}(t)$, may be determined using a reconstruction similar to the process described in FIG. 2B. Specifically, the initial post-contrast water (W') signal 308 may be projected onto the real axis 302 such that phases 212 and 318, attributed to the accumulation due to field inhomogeneity $\phi(t)$, the pre-contrast water phase $\phi_0$, and the susceptibility induced change in resonance frequency of the post-contrast water phase ($\Delta\phi_{opt}(t)$) are demodulated. The magnitude of the resultant real component vector is then taken as an estimate for the post-contrast water (W'$_{est}$) magnitude 320.

Figure 4:
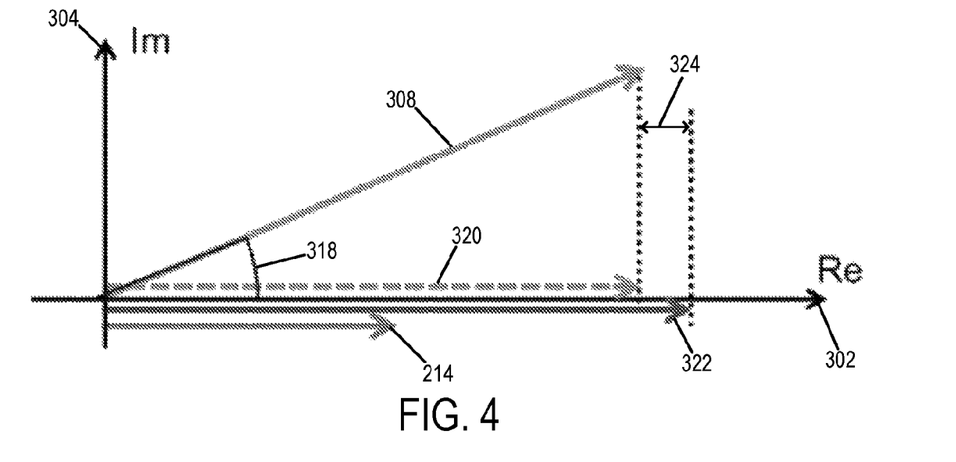
FIG. 4 is a graphical illustration of an example method for determining resonance frequency parameters from post-contrast data in accordance with an embodiments described in the present disclosure.

In some aspects, the reconstruction of the post-contrast data includes an additional processing step. In particular, referring to FIG. 4, because the additional, susceptibility induced phase ($\Delta\phi_{opt}(t)$) has further rotated the initial post-contrast water (W') signal 308 away from its initial direction parallel with the initial pre-contrast water (W) signal 208, projecting the W' signal 308 onto the real axis is equivalent to multiplying the magnitude of the W' signal 308 by $\cos(\Delta\phi_{opt}(t))$. As $\Delta\phi_{opt}(t)$ grows from zero, the cosine reduces in value from unity, diminishing the reconstructed magnitude of the water vector from its true value W'$_{opt}$ 322 to the estimated reconstructed W' value 320. This error, $\Delta W$, is depicted in FIG. 4 in as 324.

In general, the phase $\Delta\phi_{opt}(t)$ is not known because the concentration of the contrast agent is not known. However, it can be determined by iteratively applying a trial phase value $\Delta\phi_{test}(t)$ to the water channel and determining which value compensates for $\Delta\phi_{opt}(t)$ and maximizes the resultant water magnitude. That is, in some aspects, the phase of the W' signal vector 320 is adjusted by a trial phase $\Delta\phi_{test}(t)$ angle prior to projection onto the real axis 304. For example, the trial phase $\Delta\phi_{test}(t)$ may be iteratively adjusted, or calculated for a multitude of trial angles, and the trial angle that yields the maximum magnitude of the water vector along the real axis 304 is taken as the inverse of $\Delta\phi_{opt}(t)$. From knowledge of $\Delta\phi_{opt}(t)$ and the echo time (t), the frequency offset (f) and the concentration of the contrast agent may be determined, as will be described. Any of the above described parameters, pre- or post-contrast parameters, may be mapped on a voxel-wise basis across the region of interest of the subject.

Referring back to FIG. 1, once the additional phase $\phi_{opt}(t)$ is determined, one can then compute a change in resonance frequency map 110 based on the pre- and post-contrast resonance frequency values using Eqn. (7). The offset frequency can then be used to generate a contrast agent concentration map from the region of interest, as indicated in process block 112. In one aspect, the offset frequency can be converted to concentration of contrast agent using pre-determined calibration data.

Observations in accordance with the present disclosure have shown that experiments using phantoms with Gd-based contrast agents dissolved in the water-like material bovine gelatin (b-gel) cause a monotonic increase in offset frequency from that of unenhanced b-gel as the concentration of gadolinium increases. Thus, the pre-determined calibration data may comprise a linear regression between offset frequency and gadolinium concentration, which may be used to determine a gadolinium concentration given an input offset frequency value.

Figure 5:
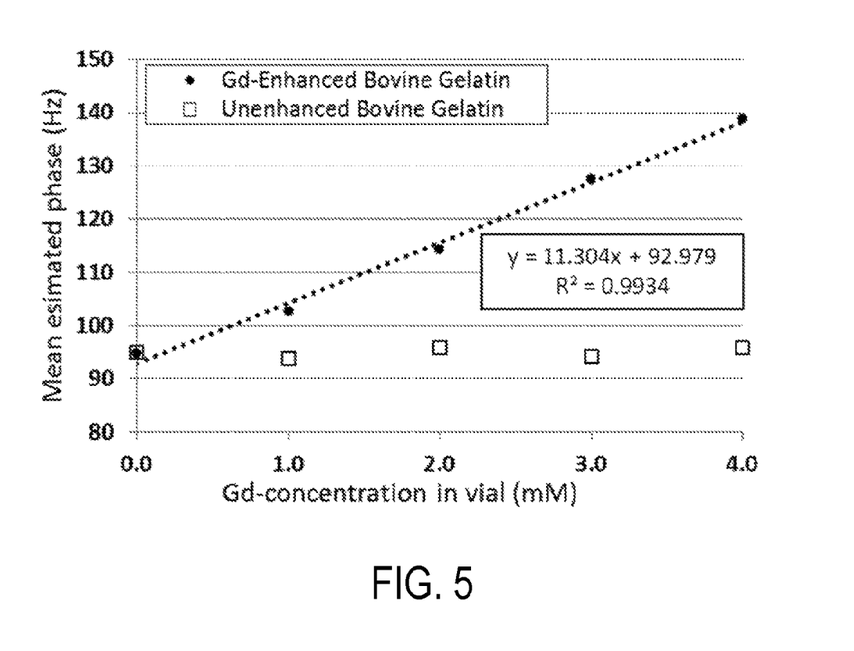
FIG. 5 is a plot of offset frequency versus the concentration of gadolinium. The plot includes a linear regression that fits the offset frequency as a function of the concentration of gadolinium.

A non-limiting example of such a calibration is shown in FIG. 5. In this case the functional dependence of offset frequency on [Gd] is given by:

$$f([Gd])(\text{in Hz}) = m \cdot [Gd] = 11.303 \cdot [Gd](\text{in mM}) \quad (8).$$

This relationship happens to be linear to a high degree of precision. This was for the specific Gd-based contrast agent Multihance. Similar calibration curves can be measured in blood for Multihance and for other agents. From knowledge of offset frequency, the concentration of gadolinium can be readily determined by inverting Eqn. (8) to solve for the concentration of gadolinium, or other contrast agents.

Other suitable contrast agents may include those that induce a phase shift after administration of the contrast agent. Non-limiting example contrast agents may include, but are not limited to, gadolinium-based contrast agents, iron-based contrast agents, and manganese-based contrast agents.

The present disclosure offers the advantage of determining the concentration of a contrast agent directly from the acquired MRI signal. Unlike other methods that rely on the change in the relaxation time T1, the present method relies on the intrinsic change caused in the resonance frequency due to the contrast agent. The method allows for the determination of the resonance frequency in each voxel prior to the arrival of the contrast agent, and for the determination of the resonance frequency when the contrast agent is present. From knowing the change in resonance frequency, a concentration of the contrast agent is determined. Advantageously, the method presented herein is not limited by uncertainties in the magnetic field inhomogeneity, because it is accounted for in the method.

Figure 6:
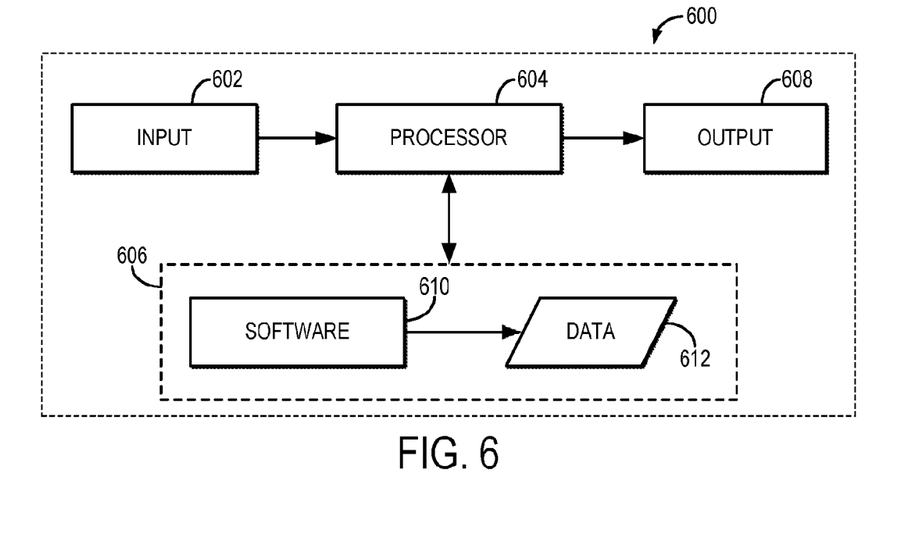
FIG. 6 is a block diagram illustrating an example of a computer system that can implement some embodiments of the present invention.

Referring now to FIG. 6, a block diagram of an example of a computer system 600 that can perform the methods described in the present disclosure is shown. The computer system 600 generally includes an input 602, at least one hardware processor 604, a memory 606, and an output 608. Thus, the computer system 600 is generally implemented with a hardware processor 604 and a memory 606.

In some embodiments, the computer system 600 can be implemented, in some examples, by a workstation, a notebook computer, a tablet device, a mobile device, a multimedia device, a network server, a mainframe, one or more controllers, one or more microcontrollers, or any other general-purpose or application-specific computing device.

The computer system 600 may operate autonomously or semi-autonomously, or may read executable software instructions from the memory 606 or a computer-readable medium (e.g., a hard drive, a CD-ROM, flash memory), or may receive instructions via the input 602 from a user, or any another source logically connected to a computer or device, such as another networked computer or server. Thus, in some embodiments, the computer system 600 can also include any suitable device for reading computer-readable storage media.

In general, the computer system 600 is programmed or otherwise configured to implement the methods and algorithms described in the present disclosure, such as those described in FIGS. 1-5. For instance, the computer system 600 can be programmed to determine the concentration of a contrast agent directly from an acquired MRI signal. In some aspects, the computer system 600 may be programmed to access acquired data from an MRI system, such as previously acquired pre-contrast data 102 and post-contrast data 104. Alternatively, the pre-contrast data 102 and the post contrast data 104 may be provided to the computer system by acquiring the data using an MRI system and communicating the acquired data to the computer system, which may be part of the MRI system.

The computer system 600 may be further programmed to process the pre- and post-contrast data to generate pre- and post-resonance frequency maps using one or more values from the pre- and post-contrast data. The computer system 600 may then generate a change in resonance frequency map based on an offset frequency change between the pre- and post-resonance frequency maps. From the change in resonance frequency map, the computer system 600 may generate a contrast agent concentration map comprising voxels that indicate a concentration of the contrast agent that was present at each voxel in the volume at the time the post-contrast data was acquired. The computer system 600 may determine the concentration of the contrast on a voxel-wise basis using the same or similar methods described in FIGS. 1-5.

The input 602 may take any suitable shape or form, as desired, for operation of the computer system 600, including the ability for selecting, entering, or otherwise specifying parameters consistent with performing tasks, processing data, or operating the computer system 600. In some aspects, the input 602 may be configured to receive data, such as data acquired with a MRI system, such as the system described in FIG. 6. Such data may be processed as described above to determine a concentration of a contrast agent from the MRI signals, or generate a contrast agent concentration map from the region of interest of the subject. In addition, the input 602 may also be configured to receive any other data or information considered useful for determining the concentration of the contrast agent using the methods described above.

Among the processing tasks for operating the computer system 600, the one or more hardware processors 604 may also be configured to carry out any number of post-processing steps on data received by way of the input 602. For example, the processor may be configured to generate a contrast agent concentration for each voxel or a concentration map based on the pre- and post-contrast data. The processor may be configured to implement the same or similar method tasks described in FIGS. 1-5.

The memory 606 may contain software 610 and data 612, such as data acquired with an MRI system, and may be configured for storage and retrieval of processed information, instructions, and data to be processed by the one or more hardware processors 604. In some aspects, the software 610 may contain instructions directed to processing the pre- and post-contrast data in order to compute a concentration of the contrast agent based on a resonance frequency change, as described in FIGS. 1-5. The software 610 may also contain instructions directed to generating a contrast-enhanced (CE) magnetic resonance angiography (MRA) image or a contrast-enhanced magnetic resonance (MR) perfusion image, and parameters associated therewith. In addition, the output 608 may take any shape or form, as desired, and may be configured for displaying the images or parameters described above.

Figure 7:
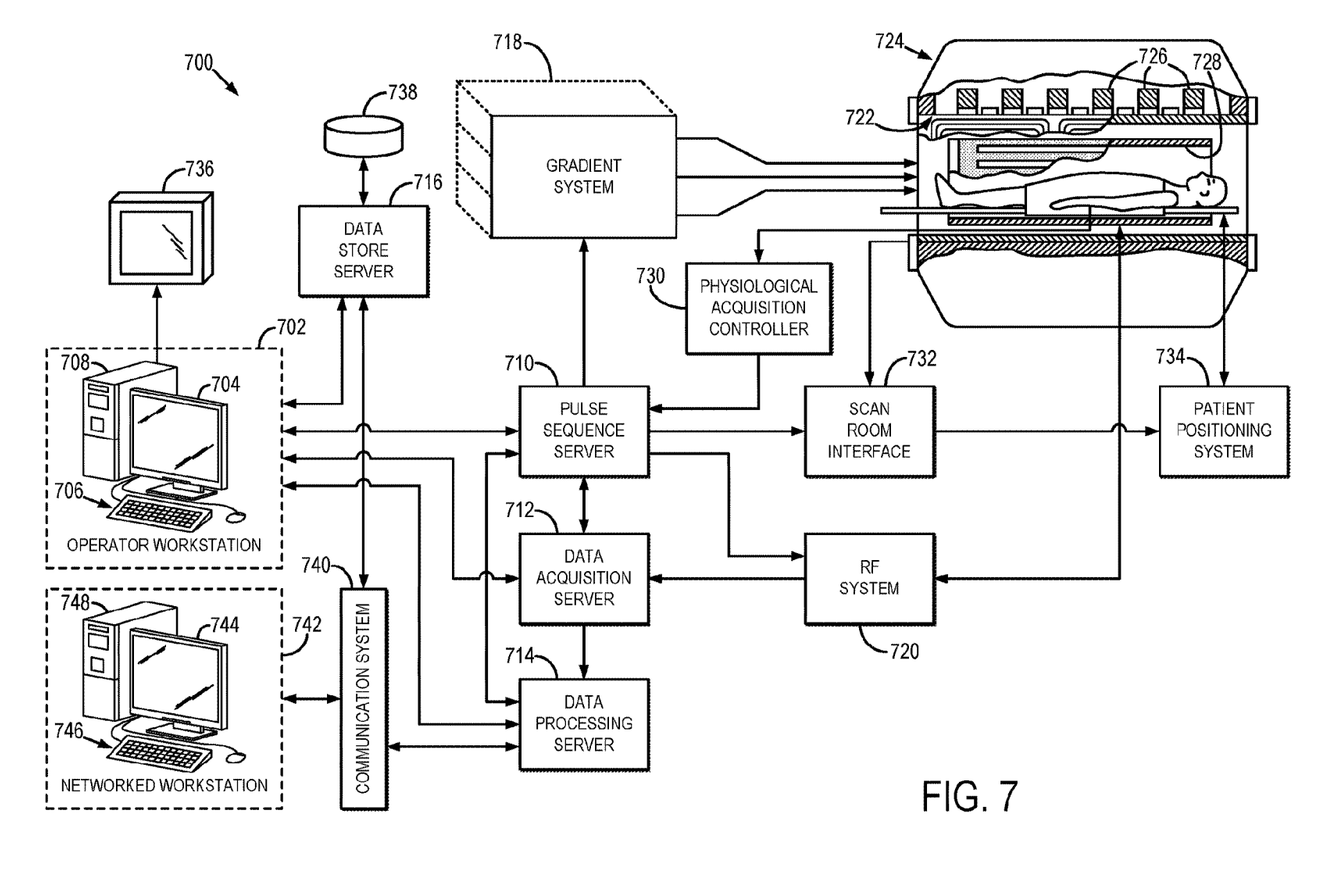
FIG. 7 is a is a block diagram of an example of a magnetic resonance imaging ("MRI") system that can implement the methods in accordance with the present disclosure.

Referring particularly now to FIG. 7, an example of an MRI system 700 that can implement the methods described here is illustrated. The MRI system 700 includes an operator workstation 702 that may include a display 704, one or more input devices 706 (e.g., a keyboard, a mouse), and a processor 708. The processor 708 may include a commercially available programmable machine running a commercially available operating system. The operator workstation 702 provides an operator interface that facilitates entering scan parameters into the MRI system 700. The operator workstation 702 may be coupled to different servers, including, for example, a pulse sequence server 710, a data acquisition server 712, a data processing server 714, and a data store server 716. The operator workstation 702 and the servers 710, 712, 714, and 716 may be connected via a communication system 740, which may include wired or wireless network connections.

The pulse sequence server 710 functions in response to instructions provided by the operator workstation 702 to operate a gradient system 718 and a radiofrequency ("RF") system 720. Gradient waveforms for performing a prescribed scan are produced and applied to the gradient system 718, which then excites gradient coils in an assembly 722 to produce the magnetic field gradients $G_x$, $G_y$, and $G_z$ that are used for spatially encoding magnetic resonance signals. The gradient coil assembly 722 forms part of a magnet assembly 724 that includes a polarizing magnet 726 and a whole-body RF coil 728.

RF waveforms are applied by the RF system 720 to the RF coil 728, or a separate local coil to perform the prescribed magnetic resonance pulse sequence. Responsive magnetic resonance signals detected by the RF coil 728, or a separate local coil, are received by the RF system 720. The responsive magnetic resonance signals may be amplified, demodulated, filtered, and digitized under direction of commands produced by the pulse sequence server 710. The RF system 720 includes an RF transmitter for producing a wide variety of RF pulses used in MRI pulse sequences. The RF transmitter is responsive to the prescribed scan and direction from the pulse sequence server 710 to produce RF pulses of the desired frequency, phase, and pulse amplitude waveform. The generated RF pulses may be applied to the whole-body RF coil 728 or to one or more local coils or coil arrays.

The RF system 720 also includes one or more RF receiver channels. An RF receiver channel includes an RF preamplifier that amplifies the magnetic resonance signal received by the coil 728 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (9);$$

and the phase of the received magnetic resonance signal may also be determined according to the following relationship:

$$\varphi = \tan^{-1}\left(\frac{Q}{I}\right). \qquad (10)$$

The pulse sequence server 710 may receive patient data from a physiological acquisition controller 730. By way of example, the physiological acquisition controller 730 may receive signals from a number of different sensors connected to the patient, including electrocardiograph ("ECG") signals from electrodes, or respiratory signals from a respiratory bellows or other respiratory monitoring devices. These signals may be used by the pulse sequence server 710 to synchronize, or "gate," the performance of the scan with the subject's heart beat or respiration.

The pulse sequence server 710 may also connect to a scan room interface circuit 732 that receives signals from various sensors associated with the condition of the patient and the magnet system. Through the scan room interface circuit 732, a patient positioning system 734 can receive commands to move the patient to desired positions during the scan.

The digitized magnetic resonance signal samples produced by the RF system 720 are received by the data acquisition server 712. The data acquisition server 712 operates in response to instructions downloaded from the operator workstation 702 to receive the real-time magnetic resonance data and provide buffer storage, so that data is not lost by data overrun. In some scans, the data acquisition server 712 passes the acquired magnetic resonance data to the data processor server 714. In scans that require information derived from acquired magnetic resonance data to control the further performance of the scan, the data acquisition server 712 may be programmed to produce such information and convey it to the pulse sequence server 710. For example, during pre-scans, magnetic resonance data may be acquired and used to calibrate the pulse sequence performed by the pulse sequence server 710. As another example, navigator signals may be acquired and used to adjust the operating parameters of the RF system 720 or the gradient system 718, or to control the view order in which k-space is sampled. In still another example, the data acquisition server 712 may also process magnetic resonance signals used to detect the arrival of a contrast agent in a magnetic resonance angiography ("MRA") scan. For example, the data acquisition server 712 may acquire magnetic resonance data and processes it in real-time to produce information that is used to control the scan.

The data processing server 714 receives magnetic resonance data from the data acquisition server 712 and processes the magnetic resonance data in accordance with instructions provided by the operator workstation 702. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 714 are conveyed back to the operator workstation 702 for storage. Real-time images may be stored in a data base memory cache, from which they may be output to operator display 702 or a display 736. Batch mode images or selected real time images may be stored in a host database on disc storage 738. When such images have been reconstructed and transferred to storage, the data processing server 714 may notify the data store server 716 on the operator workstation 702. The operator workstation 702 may be used by an operator to archive the images, produce films, or send the images via a network to other facilities.

The MRI system 700 may also include one or more networked workstations 742. For example, a networked workstation 742 may include a display 744, one or more input devices 746 (e.g., a keyboard, a mouse), and a processor 748. The networked workstation 742 may be located within the same facility as the operator workstation 702, or in a different facility, such as a different healthcare institution or clinic.

The networked workstation 742 may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may be exchanged between the data processing server 714 or the data store server 716 and the networked workstations 742, such that the data or images may be remotely processed by a networked workstation 742.

The present disclosure has described one or more preferred embodiments, and it should be appreciated that many equivalents, alternatives, variations, and modifications, aside from those expressly stated, are possible and within the scope of the invention.

The invention claimed is:

1. A method for measuring a concentration of a contrast agent using magnetic resonance imaging (MRI), the steps of the method comprising:
   (a) providing to a computer system, pre-contrast data that were acquired from a volume using an MRI system at a first time occurring before a contrast agent was present in the volume;
   (b) providing to the computer system, post-contrast data that were acquired from the volume using the MRI system at a second time occurring when the contrast agent was present in the volume;
   (c) computing from the pre-contrast data with the computer system, a pre-contrast resonance frequency map comprising voxels having values indicating first resonance frequency values for each voxel in the volume;
   (d) computing from the post-contrast data with the computer system, a post-contrast resonance frequency map comprising voxels having values indicating second resonance frequency values for each voxel in the volume, wherein the post-contrast data comprise at least post-contrast water magnitude (W') values and computing the post-contrast resonance frequency map from the post-contrast data includes:
   demodulating a phase accumulation due to field inhomogeneity, $\phi(t)$: a pre-contrast fat phase of a pre-contrast water phase $\phi_0$; and a susceptibility induced post-contrast water phase $\phi_{opt}(t)$ from the post-contrast water magnitude (W') values; and
   determining second resonance frequency values bases on the demodulated post-contrast water magnitude (W') values;
   (e) computing with the computer system, a resonance frequency change map comprising voxels having values indicating a difference between the first resonance frequency and the second resonance frequency measured at that voxel; and
   (f) generating from the resonance frequency change map, a contrast agent concentration map comprising voxels that indicate a concentration of the contrast agent that was present at each voxel in the volume at the second time.

2. The method of claim 1, wherein the pre-contrast data and the post contrast data were acquired with a gradient echo pulse sequence selected from a single-echo Dixon method or a multi-echo Dixon method.

3. The method of claim 1, wherein the pre-contrast data comprises at least two measurements acquired using a gradient echo pulse sequence, wherein the gradient echo pulse sequence is configured to acquire the two measurements at a first echo time and a second echo time occurring before the contrast agent is present in the volume.

4. The method of claim 1, wherein the post-contrast data comprises at least one measurement acquired using a gradient echo pulse sequence, wherein the gradient echo pulse sequence is configured to acquire the at least one measurement at an echo time occurring when the contrast agent is present in the volume.

5. The method of claim 1, wherein computing the pre-contrast resonance frequency map from the pre-contrast data includes determining one or more first resonance frequency value based on measured values of at least one of a pre-contrast water magnitude (W), a pre-contrast fat magnitude (F), a pre-contrast field inhomogeneity ($\Delta B_0$), and a pre-contrast water phase $\phi_W$ or a pre-contrast fat phase $\phi_F$.

6. The method of claim 5, wherein determining the one or more first resonance frequency value includes modeling the pre-contrast data signal as:

$$G(t)=(W+Fe^{i\theta(t)})e^{i(\phi(t)+\phi_0)};$$

wherein G(t) is the measured pre-contrast data signal at the first time (t), W is the pre-contrast water magnitude, $\phi_W$ is the pre-contrast water phase, F is the pre-contrast fat magnitude, $\phi_0$ is the pre-contrast fat phase or the pre-contrast water phase, $\theta(t)$ is a phase accumulation of fat due to its chemical shift with respect to water, and $\phi(t)$ is a phase accumulation due to field inhomogeneity.

7. The method of claim 5, wherein the pre-contrast water magnitude (W) is determined by projecting an initial pre-contrast water signal onto a real axis such that a phase accumulation due to field inhomogeneity ($\phi(t)$) and the pre-contrast water phase ($\phi_W$) are demodulated, and wherein the magnitude of a resultant real component vector is determined to be the pre-contrast water magnitude (W).

8. The method of claim 1, wherein determining the second resonance frequency values includes modeling the post-contrast data signal as:

$$G(t)=(W'e^{i\Delta\phi_{opt}(t)}+Fe^{i\theta(t)})e^{i(\phi(t)+\phi_0)}$$

wherein G(t) is the measured post-contrast data signal at the second time (t), W' is the post-contrast water magnitude, F is the pre-contrast fat magnitude, $\phi_{opt}(t)$ is the susceptibility induced post contrast water phase, $\phi_0$ is the post-contrast fat phase or the post-contrast water phase, θ(t) is a phase accumulation of fat due to its chemical shift with respect to water, and ϕ(t) is the phase accumulation due to field inhomogeneity.

9. The method of claim 1, wherein the post-contrast water magnitude (W') is determined by projecting an initial post-contrast water signal onto a real axis such that a pre-contrast phase (ϕ(t)+$\phi_0$) and the susceptibility induced post-contrast water phase ($\phi_{opt}(t)$) are demodulated, and wherein the magnitude of a resultant real component vector is determined to be the post-contrast water magnitude (W').

10. The method of 1, wherein the susceptibility induced post-contrast water phase ($\phi_{opt}(t)$) is determined by iterating on a trial susceptibility induced post-contrast water phase ($\phi_{test}(t)$) to project the initial post-contrast water signal until a magnitude of the resultant real component vector on the real axis is maximized.

11. The method of claim 1, wherein computing the resonance frequency change map includes determining at least one second resonance frequency value based on a measured value of the susceptibility induced post-contrast water phase ($\phi_{opt}(t)$).

12. The method of claim 11, wherein the post-contrast resonance frequency map is generated at each voxel according to:

$$f = \frac{\Delta\phi_{opt}(t)}{2\pi \cdot t};$$

wherein f is the second resonance frequency value, $\phi_{opt}(t)$ is the susceptibility induced post-contrast water phase, and t is an echo time used to acquire the post-contrast data.

13. The method of claim 1, where in the contrast agent concentration map is generated by converting values in the resonance frequency change map to contrast agent concentration using calibration data.

14. The method of claim 13, wherein the calibration data comprises a linear regression between an offset frequency and the contrast agent concentration.

15. The method of claim 1, wherein the contrast agent comprises a paramagnetic contrast agent.

16. The method of claim 15, wherein the paramagnetic contrast agent contains at least one element selected from gadolinium, manganese, and iron.

17. The method of claim 1, wherein the contrast agent concentration map is used to generate a contrast-enhanced (CE) magnetic resonance angiography (MRA) image or a contrast-enhanced magnetic resonance (MR) perfusion image.

* * * * *

UNITED STATES PATENT AND TRADEMARK OFFICE
CERTIFICATE OF CORRECTION

PATENT NO. : 11,406,277 B2
APPLICATION NO. : 16/606140
DATED : August 9, 2022
INVENTOR(S) : Stephen J. Riederer et al.

Page 1 of 1

It is certified that error appears in the above-identified patent and that said Letters Patent is hereby corrected as shown below:

In the Specification

Column 1, Lines 52-53, "subject subject" should be --subject to subject--.

Column 5, Line 38, "approximate n radians." should be --approximate $\pi$ radians--.

In the Claims

Column 14, Claim 1, Line 6, "of" should be --or--.

Column 14, Claim 1, Line 10, "bases" should be --based--.

Signed and Sealed this
Twenty-seventh Day of September, 2022

Katherine Kelly Vidal
*Director of the United States Patent and Trademark Office*